United States Patent [19]

Bayless et al.

[11] 4,182,881

[45] Jan. 8, 1980

[54] N-[DIAMINOPHOSPHINYL]ARYLCARBOX-AMIDES

[75] Inventors: Allan V. Bayless; Ozra E. Millner, Jr., both of Norwich, N.Y.

[73] Assignee: Morton-Norwich Products, Inc., Norwich, N.Y.

[21] Appl. No.: 925,968

[22] Filed: Jul. 19, 1978

[51] Int. Cl.$^2$ .................. C07D 213/00; C07D 307/46; C07F 9/22

[52] U.S. Cl. .................... 546/22; 260/347.3; 260/465 D; 260/558 R; 260/558 D; 260/558 A; 260/559 R; 424/200; 424/203; 424/210; 424/220; 424/218; 424/217

[58] Field of Search ......... 260/465 D, 558 R, 558 D, 260/558 A, 559 R, 347.3; 546/22

[56] References Cited

U.S. PATENT DOCUMENTS

| | | | |
|---|---|---|---|
| 3,317,637 | 5/1967 | Brust | 260/959 |
| 3,321,516 | 5/1967 | Popoff | 260/558 A X |
| 3,933,907 | 1/1976 | Ashton et al. | 260/558 R X |

FOREIGN PATENT DOCUMENTS 252336 7/1968 U.S.S.R. .............................. 260/558 D

OTHER PUBLICATIONS

Gadekar, et al.; J. Org. Chem., 26 (1961), p. 606.
Grayson et al., "Topics in Phosphorus Chemistry," vol. 4, 1967, pp. 350–358.
Gefter, "Organophosphorus Monomers and Polymers," 1962, p. 128.
Kosolapoff, "Organic Phosphorus Compounds," vol. 6, 1973, p. 642.
Kosolapoff, "Organophosphorus Compounds," 1950, pp. 312–315.

*Primary Examiner*—Joseph P. Brust
*Attorney, Agent, or Firm*—Anthony J. Franze

[57] ABSTRACT

A series of N-[diaminophosphinyl]arylcarboxamides are useful as inhibitors of the enzyme urease.

24 Claims, No Drawings

N-[DIAMINOPHOSPHINYL]ARYLCARBOXA-MIDES

This invention is concerned with chemical compounds. More particularly, it is concerned with a series of N-[diaminophosphinyl]arylcarboxyamides of the formula:

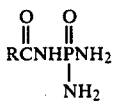

wherein R is 3-pyridyl, 2-furyl, 2-naphthyl, cinnamenyl, benzyl, phenyl or phenyl substituted by 3- or 4-nitro, 4-halo, 4-amino, 4-(lower)alkoxy, 4-(lower)alkyl, 2-methyl, 2,3-dimethyl, 2,4-dimethyl, 2,4,6-trimethyl, 3-trifluoromethyl, 4-cyano, 4-phenyl, or 3-phenoxy.

The members of this series are potent inhibitors of the enzyme urease. Urease is produced by a number of bacterial species particularly Proteus exemplary of which are *Proteus mirabilis, Proteus vulgaris, Proteus morganii* and *Proteus rettgeri*, all of which are well known urinary tract pathogens. Their ability to produce urease in the urinary tract, which contains substantial amounts of urea, provides a setting wherein urease splits urea according to this scheme:

$$H_2NCONH_2 + 2H_2O \xrightarrow{urease} 2NH_3 + H_2CO_3$$

$$2NH_3 + H_2O \rightarrow NH_4^+ + OH^-$$

This reaction sequence poses a hyperammonuria and alkalinity of the urine affording a locale favorable to the formation of struvite ($MgNH_4PO_4.6H_2O$) a predominant component of infected urinary calculi. Such struvite formation and alkalinization of the urine render the treatment of urinary tract infections difficult and oftentimes recalcitrant to otherwise effective urinary tract antiseptics.

The members of the series of compounds of this invention are highly effective in inhibiting urease which is intimately associated with the pathogenicity of the Proteus species of bacteria. Thus, a concentration of members of this series in the amount of $10^{-6}$ molar evinces an inhibition of the urease of intact *Proteus morganii* cells ranging from 14 to 100%.

The anti-urease potencies of the compounds of this invention were determined using intact *Proteus morganii* cells as the source of urease. Compounds were preincubated at $1.0 \times 10^{-6}$ moles/liter with *Proteus morganii* cells suspended in a saline solution (0.1 molar) buffered with 0.1 molar tris(hydroxymethyl)aminomethane (pH 8.0). After 40 minutes preincubation, the remaining urease activity was determined by collecting the ammonia formed in five minutes after the addition of the substrate, urea. Ammonia assays were carried out according to the procedure of Seligson and Seligson [*J. Lab. Clin. Med.* 38, 324–330 (1951)]. Percent inhibition was calculated by comparing the amount of ammonia generated by cells preincubated with $1 \times 10^{-6}$ molar compound with the controls, in which preincubation was carried out in the absence of compound.

The method currently preferred for the preparation of the compounds of this invention is represented by the following schema:

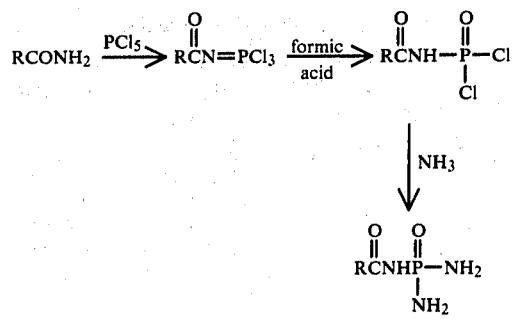

wherein R has the aforementioned significance except in the case of amino which is prepared by catalytic reduction of the corresponding nitro compound. The appended examples are further illustrative of the making of the compounds of this invention.

The members of the series of compounds of this invention are readily formulated in classical pharmaceutical dosage forms such as tablets, elixirs, suspensions, capsules, solutions, dragees and the like employing excipients, adjuvants and additives known to the apothecary art and with which there is no incompatibility.

EXAMPLE I

N-[Diaminophosphinyl]benzamide 11.9 g (0.05 mole) of N-[dichlorophosphinyl]benzamide was dissolved in 90 ml of reagent $CHCl_3$. A small amount of solid was filtered off, and the solution was added dropwise over 2 hrs. to a vigorously stirred solution of 7 g (0.41 mole) of $NH_3$ in 200 ml of $CHCl_3$ which was cooled in an ice bath. $NH_3$ was bubbled in during the addition. The reaction was stirred a further 0.5 hr., and was filtered to yield 14 g of solid. This was washed with water (to get rid of $NH_4Cl$) to give 7.5 g (75%), m.p. foams ~380°. 6 g of this was recrystallized from ~70 ml of boiling water to yield an analytical sample of 4.95 g, m.p. foams >380°; appears to dehydrate >200°.

Anal. Calcd. for $C_7H_{10}N_3O_2P$: C, 42.21; H, 5.06; N, 21.10. Found: C, 41.88; H, 5.01; N, 20.91.

EXAMPLE II

N-(Diaminophosphinyl)-3-pyridinecarboxamide

To a suspension of 36.63 g (0.30 mole) of nicotinamide in 400 ml of reagent chloroform was added 62.5 g (0.30 mole) of phosphorus pentachloride. The reaction was refluxed with stirring for 2 hrs., by which time HCl evolution had essentially ceased. It was cooled to R.T., and 15.7 g of formic acid (88%, 0.30 mole) was added portionwise over 15 min. with vigorous stirring. It was stirred for 20 hrs. at R.T., then for 10 min. on a steam bath. A sample was filtered off for analysis.

Anal. Calcd. for $C_6H_5N_2O_2PCl_2$: C, 30.15; H, 2.11; N, 11.72. Found: C, 30.99; H, 4.36; N, 12.17.

The reaction then was stirred vigorously in an ice bath for 1 hr. while $NH_3$ gas was blown in. It was stirred a further 1 hr. while warming to R.T., and was filtered to yield 131 g of lt. tan solid. This was suspended in 200 ml of $H_2O$, and 30 ml of conc. $NH_4OH$ solution was added. Filtered to yield 12.2 g (20%). Recrystallization from 100 ml of boiling water gave 9.15 g, m.p. "dehydrates" ~200°, dec. >290°.

Anal. Calcd. for $C_6H_9N_4O_2P$: C, 36.00; H, 4.53; N, 28.00. Found: C, 35.84; H, 4.48; N, 28.08.

EXAMPLE III

N-[Diaminophosphinyl]-4-nitrobenzamide

A. N-[Dichlorophosphinyl]-4-nitrobenzamide

To a suspension of 68 g (0.41 mole) of 4-nitrobenzamide in 400 ml of AR carbon tetrachloride at 48° was added portionwise 85.2 g (0.41 mole) of phosphorus pentachloride. The reaction was heated at 65°–70° for 50 min., then cooled to 25°–30°. Added dropwise while maintaining a temperature of 30°, 19.4 g (0.41 mole) of 97% formic acid. After the evolution of gas (CO and HCl) had ceased the reaction was filtered, washed with AR carbon tetrachloride and air-dried to give 103.2 g, m.p. 134°–135.5°.

B. N-[Diaminophosphinyl]-4-nitrobenzamide

To a suspension of 14.2 g (0.25 mole) of N-[dichlorophosphinyl]-4-nitrobenzamide in 150 ml of AR chloroform was added 8.5 g (0.5 mole) of anhydrous ammonia, while maintaining a temperature of 0°. (Addition time 30 min.) After stirring for 90 min., the reaction was filtered, washed with cold water and air-dried to give 13 g, m.p. softens 180°, >400°. One re-recrystallization from 500 ml of distilled water with Darco gave 7.4 g, m.p. softens 180°, melts >400°. This was combined with 20 g of crude product and recrystallized from 800 ml of methanol containing 400 ml of distilled water, with Darco, to yield 15.95 g (13%), m.p. >400°.

Anal. Calcd. for $C_7H_9N_4O_4P$: C, 34.43; H, 3.72; N, 22.95. Found: C, 34.56; H, 3.78; N, 23.08.

EXAMPLE IV

N-[Diaminophosphinyl]-4-fluorobenzamide

A. N-[Dichlorophosphinyl]-4-fluorobenzamide

A mixture of 19.5 g (0.14 mole) of 4-fluorobenzamide, 29.2 g (0.14 mole) of phosphorus pentachloride and 175 ml of carbon tetrachloride was heated at 60°–70° for 30 min. or until the HCl gas evolution had nearly stopped. The reaction was cooled to 25°–30° and 6.7 g (0.14 mole) of 97% formic acid was added dropwise. Stirring was continued for another 60 min. before the precipitate was collected by filtration, washed with AR carbon tetrachloride and air-dried to give 20.4 g, m.p. softens 109°, melts 110°–112°.

B. N-[Diaminophosphinyl]-4-fluorobenzamide

Added 13.3 g (0.78 mole) of anhydrous ammonia to a suspension of 20 g (0.078 mole) of N-[dichlorophosphinyl]-4-fluorobenzamide in 150 ml of AR chloroform. A temperature of 0° was maintained throughout the 30 min. addition. After stirring for 60 min., the crude product was filtered, washed with water and dried to give 17 g, m.p. softens 230°, melts >400°. Recrystallization from 425 ml of distilled water, with Darco, yielded 9.9 g (58%), m.p. shrinks 300°, melts >400°.

Anal. Calcd. for $C_7H_9FN_3O_2P$: C, 38.72; H, 4.18; N, 19.25. Found: C, 38.71; H, 4.24; N, 19.44.

EXAMPLE V

4-Amino-N-[diaminophosphinyl]benzamide 30 g (0.12 mole) of N-[diaminophosphinyl]-4-nitrobenzamide in 800 ml of absolute alcohol was reduced using 4.0 g of 5% Pd/C containing 50% water. A hydrogen uptake of 19.9 psi. was recorded after 60 hr. (theoretical 24 psi.). Added 2000 ml of absolute alcohol and 2000 ml of dimethylformamide to dissolve. The catalyst was removed by filtration and the filtrate flash-evaporated down to 125 ml. Chilled to 0°, filtered and washed with anhydrous ethyl ether to yield 12.4 g (48%), m.p. darkens 168°–172°, softens 290°, decomposes 340°.

Anal. Calcd. for $C_7H_{11}N_4O_2P$: C, 39.25; H, 5.18; N, 26.16. Found: C, 39.13; H, 5.27; N, 26.03.

EXAMPLE VI

N-[Diaminophosphinyl]-4-chlorobenzamide

A. 4-Chloro-N-[dichlorophosphinyl]benzamide

A suspension of 68 g, (0.44 mole) of 4-chlorobenzamide, 91 g (0.44 mole) of phosphorus pentachloride and 700 ml of AR carbon tetrachloride was heated at 65°–70° for 25 min. The solution was cooled to 20° and 20.7 g (0.44 mole) of 97% formic acid added dropwise. After the HCl gas evolution had nearly stopped, ca. 30 min., the precipitate was collected by filtration, washed with AR carbon tetrachloride and air-dried to give 103 g, m.p. 114.5°–115.5°.

B. N-[Diaminophosphinyl]-4-chlorobenzamide

To a suspension of 103 g (0.38 mole) of 4-chloro-N-[dichlorophosphinyl]benzamide in 1000 ml of AR chloroform was added 65 g (3.8 mole) of anhydrous ammonia. A temperature of 0° was maintained over the 30 min. addition period. After stirring for 60 min., the crude product was filtered, washed with cold distilled water and air-dried to give 81 g. Recrystallization from 3000 ml of distilled water gave a yield of 48 g (54%), m.p. softens, shrinks 182°–340°.

Anal. Calcd. for $C_7H_9ClN_3O_2P$: C, 35.99; H, 3.88; N, 17.99. Found C, 36.04; H, 3.89; N, 17.83.

EXAMPLE VII

N-[Diaminophosphinyl]-3-nitrobenzamide

Added 42.6 g (2.5 mole) of anhydrous ammonia to a suspension of 65 g (0.25 mole) of N-[dichlorophosphinyl]-2-nitrobenzamide in 600 ml of AR chloroform while maintaining a temperature of 0°. Stirred for another 30 min. following the 30 min. addition, then collected the white precipitate by filtration, washed with water and air-dried. The 54 g of crude product was recrystallized from 300 ml of distilled water, with Darco, to yield 36 g (59%), m.p. 168°–172°. r-dried. The 54 g of crude product was recrystallized from 300 ml of distilled water, with Darco, to yield 36 g (59%), m.p. 168°–172°.

Anal. Calcd. for $C_7H_9N_4O_4P$: C, 34.43; H, 3.72; N, 22.95. Found: C, 34.50; H, 3.86; N, 22.69.

EXAMPLE VIII

N-[Diaminophosphinyl]-4-methoxybenzamide

A. N-[Dichlorophosphinyl]-4-methoxybenzamide

A suspension of 47 g (0.31 mole) of 4-methoxybenzamide, 64.7 g (0.31 mole) of phosphorus pentachloride and 500 ml of AR carbon tetrachloride was heated at 60°–70° for 45 min. by which time the HCl evolution had nearly stopped. Cooled to room temperature where 14.8 g (0.31 mole) of 97% formic acid was added dropwise. The reaction was stirred for an additional 30 min., then filtered, washed with AR carbon tetrachloride and air-dried to give 73.4 g, m.p. 92°–93°.

B. N-[Diaminophosphinyl]-4-methoxybenzamide

To a mixture of 73.4 g (0.27 mole) of N-[dichlorophosphinyl]-4-methoxybenzamide in chloroform was added anhydrous ammonia until 46 g (2.7 mole) had been absorbed. A temperature of 0° was maintained throughout the 33 min. addition. The white precipitate was collected, washed with cold distilled water and recrystallized from 300 ml of distilled water, with Darco, to give 6.9 g, m.p. softens, shrinks 170°, 190°–303°, melts >400°. Another recrystallization from 500 ml of methanol, with Darco, gave 3.93 g (6.4%), m.p. softens 188°, decomposes 310°–372°.

Anal. Calcd. for $C_8H_{12}N_3O_3P$: C, 41.92; H, 5.28; N, 18.34. Found: C, 42.20; H, 5.32; N, 18.44.

EXAMPLE IX

N-[Diaminophosphinyl]-4-methylbenzamide

A. N-[dichlorophosphinyl]-4-methylbenzamide

A mixture of 53 g (0.39 mole) of 4-methylbenzamide, 81.7 g (0.39 mole) of phosphorus pentachloride and 500 ml of AR carbon tetrachloride was heated at 60°–70° until the HCl gas evolution had ceased. Solution was cooled to 30° where 18.6 g (0.39 mole) of 97% formic acid was added. Continued to stir for 30 min. following the addition, then filtered, washed with AR carbon tetrachloride and air-dried to give 74.5 g, m.p. 96.5°–98°.

B. N-[Diaminophosphinyl]-4-methylbenzamide

To a mixture of 74.5 g (0.3 mole) of N-[dichlorophosphinyl]-4-methylbenzamide in 750 ml of AR chloroform at 0° was passed anhydrous ammonia until 51 g (3.0 mole) had been absorbed, ca. 35 min. Stirring was continued for another 30 min. before the precipitate was collected, washed with cold distilled water and then recrystallized from 400 ml of boiling distilled water, with Darco, to give 18.1 g, m.p. softens 120°, slow melt to 400°. Recrystallized a second time from 500 ml of methanol, with Darco, to yield 5.9 g (9%), m.p. softens 270°, decomposes to 400°.

Anal. Calcd. for $C_8H_{12}N_3O_2P$: C, 45.07; H, 5.67; N, 19.71. Found: C, 44.94; H, 5.81; N, 19.37.

EXAMPLE X

N-[Diaminophosphinyl]-2-methylbenzamide

A. N-[Dichlorophosphinyl]-2-methylbenzamide

A mixture containing 48 g (0.36 mole) of 2-methylbenzamide, 74 g (0.36 mole) of phosphorus pentachloride and 500 ml of AR carbon tetrachloride was heated at 60°–70° for 30 min. at which time the HCl gas evolution had ceased. The solution was cooled to 30° and 16.9 g (0.36 mole) of 97% formic acid added dropwise. Stirring was continued following the addition for 40–50 min. The product was colleted, washed with AR carbon tetrachloride and air-dried to give 56 g, m.p. 91°–93°.

B. N-[Diaminophosphinyl]-2-methylbenzamide

Anhydrous ammonia was added to a suspension of 56 g (0.22 mole) of N-[dichlorophosphinyl]-2-methylbenzamide in chloroform at 0° until 37.5 g (2.2 mole) had been absorbed. The crude product was filtered, washed thoroughly with cold water and air-dried to give 34.1 g, m.p. softens 120°, slow melt at 400°. A recrystallization from 800 ml of methanol, with Darco, followed by a recrystallization from 100 ml of distilled water, with Darco, yielded 9.2 g (20%), m.p. softens 162°, decomposes 310°–348°.

Anal. Calcd. for $C_8H_{12}N_3O_2P$: C, 45.07; H, 5.67; N, 19.71. Found: C, 45.03; H, 5.73; N, 19.52.

EXAMPLE XI

4-Cyano-N-[diaminophosphinyl]benzamide

A. 4-Cyano-N-[dichlorophosphinyl]benzamide

A suspension of 18.1 g (0.12 mole) of 4-cyanobenzamide, 25.8 g (0.12 mole) of phosphorus pentachloride and 250 ml of AR carbon tetrachloride was stirred and heated at 70° until the HCl gas evolution had subsided; ca. 25 min. The solution was cooled to 30° and 5.9 g (0.12 mole) of 97% formic acid was added while maintaining a temperature of 30°. After stirring for 30 min., the product was collected, washed with AR carbon tetrachloride and dried to give 52 g, m.p. shrinks 162°–165°, darkens 218°, decomposes >300°.

B. 4-Cyano-N-[diaminophosphinyl]benzamide

A mixture of 52 g (0.2 mole) of 4-cyano-N-[dichlorophosphinyl]benzamide and 500 ml of AR chloroform was chilled to 0° and anhydrous ammonia was added until 33.7 g (2.0 mole) had been absorbed. Stirring was continued for 30 min., then the reaction filtered, washed with cold water and air-dried to give 17.3 g. Recrystallized from 800 ml of distilled water, with Darco, followed by a recrystallization from 1000 ml of methanol, with Darco, to yield 12.5 g (28%), m.p. shrinks 198°, softens 240°, decomposes to 400°.

Anal. Calcd. for $C_8H_9N_4O_2P$: C, 42.86; H, 4.05; N, 25.00. Found: C, 43.38; H, 4.07; N, 25.28.

EXAMPLE XII

N-[Diaminophosphinyl]-3-trifluoromethylbenzamide

A. N-[Dichlorophosphinyl]-3-trifluoromethylbenzamide

A suspension of 15 g (0.08 mole) of 3-trifluoromethylbenzamide, 16.5 g (0.08 mole) of phosphorus pentachloride and 150 ml of AR carbon tetrachloride was heated at 65°–70° until the HCl gas evolution nearly stops, ca. 30 min. The solution was cooled to 30° and 3.8 g (0.08 mole) of 97% formic acid added dropwise. Stirring was continued for 30 min., then the precipitate was collected, washed with AR carbon tetrachloride and air-dried to give 14 g, m.p. softens 112°, melts 114°–116°.

B. N-[Diaminophosphinyl]-3-trifluoromethylbenzamide

Added 7.8 g (0.46 mole) of anhydrous ammonia to a solution of 14 g (0.046 mole) of N-[dichlorophosphinyl]-3-trifluoromethylbenzamide in 150 ml of AR chloroform. A temperature of 0° was maintained through the 30 min. addition. After stirring for another 30 min. following the addition, the product was filtered, washed with AR chloroform and air-dried to give 17.8 g, m.p. softens 135°, shrinks 150°, decomposes 292°–300°. One recrystallization from methanol, with Darco, followed by two recrystallizations from water, with Darco, yielded 4.7 g (38%), m.p. softens 143°, most melts 153°–157°, solidifies, decomposes 250°–400°.

Anal. Calcd. for $C_8H_9F_3N_3O_2P$: C, 35.97; H, 3.40; N, 15.73. Found: C, 35.71; H, 3.39; N, 15.76.

EXAMPLE XIII

N-[Diaminophosphinyl]-4-[1,1-dimethylethyl]benzamide

A. N-[Dichlorophosphinyl]-4-[1,1-dimethylethyl]benzamide

A mixture of 75 g (0.42 mole) of 4-tert-butylbenzamide, 88.1 g (0.42 mole) of phosphorus pentachloride and 750 ml of AR carbon tetrachloride was heated at 70° until the evolution of HCl had nearly ceased. The reaction was cooled to 30° and 19.5 g (0.42 mole) of 97% formic acid, added dropwise. After the 20 min. addition, it was chilled to 0°, filtered, washed with AR carbon tetrachloride and air-dired to give 82 g, m.p. 110°–111°.

B. N-[Diaminophosphinyl]-4-[1,1-dimethylethyl]benzamide

A solution of 82 g (0.28 mole) of N-[dichlorophosphinyl]-4-[1,1-dimethyethyl]benzamide in 800 ml of AR chloroform was chilled to 0° where 47.5 g (2.8 mole) of anhydrous ammonia was added. Continued stirring for 30 min. following the addition. Collected the white precipitate by filtration, washed with cold water and air-dried to give 48 g, m.p. softens 148°, melts 160°, solidifies, darkens 258°, >400°. Recrystallized from 2500 ml of distilled water, with Darco, to give 19.3 g. Another recrystallization from 1000 ml of distilled water, with Darco, gave 12.5 g, m.p. shrinks 175°, melts at 232°. A third recrystallization from 75 ml of methanol, with Darco, gave a yield of 6.1 g (9.0%), m.p. softens 173°, melts 182°–185°, solidifies >400°.

Anal. Calcd. for $C_{11}H_{18}N_3O_2P$: C, 51.76; H, 7.11; N, 16.46. Found: C, 51.96; H, 7.05; N, 16.35.

EXAMPLE XIV

N-[Diaminophosphinyl]-2-naphthalenecarboxamide

A. N-[Dichlorophosphinyl]-2-naphthamide

A mixture of 40 g (0.23 mole) of 2-naphthalene carboxamide, 48.7 g (0.23 mole) of phosphorus pentachloride and 400 ml of AR carbon tetrachloride was heated at 70° for 30 min. at which time the HCl evolution had ceased. It was cooled to 30° and 11.1 g (0.23 mole) of 97% formic acid added dropwise. Continued to stir for 30 min., then filtered, washed with AR carbon tetrachloride and air-dried to give 43 g, m.p. 110°–111°.

B. N-[Diaminophosphinyl]-2-naphthalenecarboxamide

A solution of 43 g (0.15 mole) of N-[dichlorophosphinyl]-2-naphthamide in 400 ml of AR chloroform was chilled to 0° where 25.4 g (1.5 mole) of anhydrous ammonia was added over 20 min. After stirring an additional 30 min. At 0°, the reaction was filtered, washed with cold water and air-dried to give 33.1 g, m.p. softens 180°, melts 182°, solidifies, melts >400°. Triturated in 750 ml of methanol followed by a trituration in hot AR chloroform to give 23 g, m.p. >400°. Stirred in 500 ml of distilled water for 36 hrs., filtered and air-dried to give 14 g. Attempted to dissolved in a mixture of 3500 ml of methanol and 300 ml of water. Filtered hot and air-dried the insolubles to yield 5.8 g (16%), m.p. softens 230°, decomposes 232°–400°. Recovered another 0.9 g from the filtrate, m.p. softens 232°, decomposes to 400°.

Anal. Calcd. for $C_{11}H_{12}N_3O_2P$: C, 53.01; H, 4.85; N, 16.86. Found: C, 53.08; H, 4.86; N, 16.17.

EXAMPLE XV

N-[Diaminophosphinyl]benzeneacetamide

A. N-[Dichlorophosphinyl]benzeneacetamide

A suspension of 50 g (0.37 mole) of phenylacetamide, 77 g (0.37 mole) of phosphorus pentachloride and 500 ml of AR carbon tetrachloride was heated at 70° for 25 min. or until the HCl gas evolution ceases. The resulting solution was cooled to 30°, then 17.6 g (0.37 mole) of 97% formic acid was added, dropwise. Stirred at 30° for 30 min. following the addition, then filtered, washed with AR carbon tetrachloride and air-dried to give 80 g, m.p. softens 79°, some melts 83°–94°, complete 120°.

B. N-[Diaminophosphinly]benzeneacetamide

To a suspension of 80 g (0.32 mole) of N-[dichlorophosphinyl]benzeneacetamide in 800 ml of AR chloroform was added, over 20–30 min., 54.1 g (3.2 mole) of anhydrous ammonia while maintaining a temperature of 0°. Stirring was continued for 30 min. then the precipitate was collected by filtration, washed thoroughly with cold water and air-dried to give 81 g, m.p. shrinks 192°, darkens 258°, softens 360°, melts 400°. Two recrystallizations from distilled water, with Darco, gave a yield of 15.1 g (22%), m.p. darkens 270°, melts >400°.

Anal. Calcd. for $C_8H_{12}N_3O_2P$: C, 45.07; H, 5.67; N, 19.71. Found: C, 44.89; H, 5.66; N, 19,67.

EXAMPLE XVI

N-[Diaminophosphinyl]-2,3-dimethylbenzamide

A. N-[Dichlorophosphinyl]-2,3-dimethylbenzamide

Heated at 70° for 30 min. a mixture containing 23.3 g (0.16 mole) of 2,3-dimethylbenzamide, 32.5 g (0.16 mole) of phosphorus pentachloride and 250 ml of AR carbon tetrachloride. The resulting solution was cooled to 30° and 7.4 g (0.16 mole) of 97% formic acid added. Continued to stir at 30° for 20 min. then chilled to 0°, filtered, washed with AR carbon tetrachloride and air-dried to give 36.1 g, m.p. 88°–90°.

B. N-[Diaminophosphinyl]-2,3-dimethylbenzamide

To a suspension of 36 g (0.14 mole) of N-[dichlorophosphinyl]-2,3-dimethylbenzamide in 400 ml of AR chloroform was added 23 g (1.4 mole) of anhydrous ammonia while maintaining a temperature of 0°. The white precipitate was collected by filtration, washed with cold water and air-dried to give 22 g, m.p. softens 151°, some melts 174°, decomposes 350°–400°. One recrystallization from distilled water, with Darco, and two recrystallizations from methanol, with Darco, gave a yield of 1.9 g (6%), m.p. softens 177°, 317°, decomposes >400°.

Anal. Calcd. for $C_9H_{14}N_3O_2P$: C, 47.57; H, 6.21; N, 18.50. Found: C, 47.61; H, 6.36; N, 18.40.

EXAMPLE XVII

N-[Diaminophosphinyl]-3-phenoxybenzamide

A. 3-Phenoxybenzoyl Chloride

Added portionwise 25 g (0.12 mole) of 3-phenoxybenzoic acid, to 125 ml of thionyl chloride, then heated at reflux for 2 hrs. The solution was distilled to remove the excess thionyl chloride. Added 200 ml of AR toluene and evaporated in vacuo to give 23 g of red liquid.

B. 3-Phenoxybenzamide

Saturated with anhydrous ammonia a solution containing 23 g (0.1 mole) of 3-phenoxybenzoyl chloride and 250 ml of AR chloroform. Continued stirring for 30 min., chilled to 0° and filtered. The product was pulverised, triturated in cold water and oven-dried to give 21.3 g, m.p. 127°–128°.

C. N-[Dichlorophosphinyl]-3-phenoxybenzamide

A mixture containing 21.3 g (0.1 mole) of 3-phenoxybenzamide, 20.8 g (0.1 mole) of phosphorus pentachloride and 250 ml of Ar carbon tetrachloride was heated at 70° for 30 min. The resulting solution was cooled to 30° and 4.7 g (0.1 mole) of 97% formic acid added dropwise. Stirring was continued for 20 min., the reaction was filtered, washed with AR carbon tetrachloride and air-dried to give 31 g, m.p. 122°–125°.

D. N-[Diaminophosphinyl]-3-phenoxybenzamide

To 31 g (0.1 mole) of N-[dichlorophosphinyl]-3-phenoxybenzamide in 300 ml of AR chloroform was added 16.7 g (1.0 mole) of anhydrous ammonia. A temperature of 0° was maintained through the addition. The reaction was stirred another 30 min., then filtered, washed thoroughly with cold water and air-dried. The 21.5 g of crude product was recrystallized from 450 ml of methanol, with Darco, to yield 10.8 g (37%), m.p. shrinks 170°, decomposes 174°–176°.

Anal. Calcd. for $C_{13}H_{14}N_3O_3P$: C, 53.61; H, 4.85; N, 14.43. Found: C, 53.57; H, 4.88; N, 14.44.

EXAMPLE XVIII

4-Butoxy-N-[diaminophosphinyl]benzamide

A. 4-n-Butoxybenzoyl Chloride

Heated at reflux a solution of 75 g (0.39 mole) of 4-n-butoxybenzoic acid in 250 ml of thionyl chloride for 3 hrs. Removed by vacuum distillation the excess thionyl chloride to give 84 g of a brown colored liquid.

B. 4-n-Butoxybenzamide

Chilled to 20°, a solution of 84 g (0.39 mole) of a solution of 4-n-butoxybenzoyl chloride in 700 ml of AR chloroform, then saturated with anhydrous ammonia. The mixture was stirred for 20 min. to 0°, then the white precipitate collected, washed with cold water and oven-dried to 60° to give 76 g, m.p. shrinks 160°, melts 162°–164°.

C. 4-Butoxy-N-[dichlorophosphinyl]benzamide

A mixture of 76 g (0.39 mole) of 4-butoxybenzamide, 81.9 g (0.39 mole) of phosphorus pentachloride and 700 ml of AR carbon tetrachloride was heated at 70° for 30 min. The resulting solution was cooled to 30° and 18.7 g (0.39 mole) of 97% formic acid was added. The reaction was chilled to 0°, filtered, washed with AR carbon tetrachloride and air-dried to give 52.1 g, m.p. 97°–98°.

D. 4-Butoxy-N-[diaminophosphinyl]benzamide

To a mixture of 52.1 g (0.17 mole) of 4-butoxy-N-[dichlorophosphinyl]benzamide in 500 ml of AR chloroform was added 28.6 g (1.7 mole) of anhydrous ammonia while maintaining a temperature of 0°. The reaction was filtered, the residue triturated in cold water and again filtered. Recrystallization from 500 ml of AR methanol, with Darco, gave 8.9 g (19%), m.p. melts 174°–178°, solidifies, darkens 290°, decomposes 280°–400°.

Anal. Calcd. for $C_{11}H_{18}N_3O_3P$: C, 48.70; H, 6.69; N, 15.49. Found: C, 48.76; H, 6.71; N, 15.32.

EXAMPLE XIX

N-[Diaminophosphinyl]-3-phenyl-2-propenamide

A. N-[Dichlorophosphinyl]cinnamamide

Heated at 70° for 25 min. at which time the HCl gas evolution had ceased, a mixture of 59 g (0.4 mole) of cinnamide, 83.5 g (0.4 mole) of phosphorus pentachloride and 500 ml of AR carbon tetrachloride. After cooling to 30°, added dropwise, 19 g (0.4 mole) of 97% formic acid. Chilled to 0° and filtered. Air-dried to give 107.5 g, m.p. softens 82°, melts 83°–90°.

B. N-[Diaminophosphinyl]-3-phenyl-2-propenamide

To a suspension of 107 g (0.41 mole) of N-[dichlorophosphinyl]-cinnamamide in 1000 ml of AR chloroform was added 69 g (4.1 mole) of anhydrous ammonia while maintaining a temperature of 0°. The white precipitate was collected by filtration, washed with cold, distilled water and air-dried. Two recrystallizations from methanol, with Darco, gave a yield of 9.9 g (10%), m.p. decomposes 184°–189°.

Anal. Calcd. for $C_9H_{12}N_3O_2P$: C, 48.00; H, 5.37; N, 18.66. Found: C, 47.79; H, 5.43; N, 18.54.

EXAMPLE XX

N-[Diaminophosphinyl]-4-phenylbenzamide

A. 4-Biphenylcarbonyl Chloride

Heated at reflux for 2 hrs., a solution of 25 g (0.13 mole) of 4-biphenylcarboxylic acid, in 125 ml of thionyl chloride. Distilled to remove the excess thionyl chloride, then added 150 ml of AR toluene. Evaporated in vacuo to give a brown solid, 27 g, m.p. softens 107°, some melts 109°–112°, darkens 370°, melts >400°.

B. 4-Phenylbenzamide

A mixture of 27 g (0.12 mole) of 4-biphenylcarbonyl chloride and 300 ml of AR chloroform was saturated with anhydrous ammonia while maintaining a temperature of 20°. Following the 20 min. addition the white precipitate was collected, washed with cold water and oven-dried (60°) to give 23.5 g, m.p. shrinks 228°, melts 230°–233°.

C. N-[Dichlorophosphinyl]-4-phenylbenzamide

A mixture of 23.5 g (0.12 mole) of 4-phenylbenzamide, 24.8 g (0.12 mole) of phosphorus pentachloride and 250 ml of AR carbon tetrachloride was heated at 70° until the HCl gas evolution nearly stops. It was chilled to 30° and 5.7 g (0.12 mole) of 97% formic acid added dropwise. The precipitate was collected, washed with AR carbon tetrachloride and air-dried to give 3.1 g, m.p. 123°–124°.

D. N-[Diaminophosphinyl]-4-phenylbenzamide

To a suspension of 31.1 g (0.1 mole) of N-[dichlorophosphinyl]-4-phenylbenzamide in 300 ml of AR chloroform at 0° was added over 20 min., 17 g (1.0 mole) of anhydrous ammonia. Continued stirring for 20 min. following the addition. The reaction was filtered, washed with cold water and air-dried. The 29 g of crude product was recrystallized from 3000 ml of methanol to yield 3.1 g (11%), m.p. decomposes 214°–221°, solidifies, decomposes 248°–400°.

Anal. Calcd. for $C_{13}H_{14}N_3O_2P$: C, 56.72; H, 5.13; N, 15.27. Found: C, 56.97; L H, 5,19; N, 15.18.

EXAMPLE XXI

N-[Diaminophosphinyl]-2,4-dimethylbenzamide

A. 2,4-Dimethylbenzamide

Saturated with anhydrous ammonia, a solution of 50 g (0.3 mole) of 2,4-dimethylbenzoyl chloride and 500 ml of AR chloroform, while maintaining a temperature of 15°. Stirred for 20 min., then filtered, washed with cold distilled water and oven-dried at 60° to give 29.1 g, m.p. 184°–186°.

B. N-[Dichlorophosphinyl]-2,4-dimethylbenzamide

A suspension of 29 g (0.19 mole) of 2,4-dimethylbenzamide, 40.5 g (0.19 mole) of phosphorus pentachloride and 300 ml of AR carbon tetrachloride was heated at 70° for 30 min. The solution was cooled to 30° and 9.2 g (0.19 mole) of 97% formic acid added dropwise. Stirring was continued for another 20 min., then the product was collected by filtration, washed with AR carbon tetrachloride and air-dried to give 30.5 g, m.p. decomposes upon standing.

C. N-[Diaminophosphinyl]-2,4-dimethylbenzamide

Added 19.5 g (1.1 mole) of anhydrous ammonia to a chilled (0°) mixture of 30.5 g (0.11 mole) of N-[dichlorophosphinyl]-2,4-dimethylbenzamide in 300 ml of AR chloroform. Kept at 0° for an additional 30 min., then evaporated to dryness in vacuo. The residue was dissolved in 250 ml of boiling distilled water to give 8.7 g, m.p. softens 110°, some melts 136°–150°, solidifies, decomposes 249°–400°. Three recrystallizations from methanol, with Darco, gave a yield of <1.0 g (4%), m.p. softens 175°, darkens 325°, decomposes to 400°.

Anal. Calcd. for $C_9H_{14}N_3O_2P$: C, 47.57; H, 6.21; N, 18.50. Found: C, 47.80; H, 6.27; N, 17.71.

EXAMPLE XXII

N-[Diaminophosphinyl]-2,4,6-trimethylbenzamide

A. 2,4,6-Trimethylbenzoyl Chloride

A solution of 50 g (0.3 mole) of 2,4,6-trimethylbenzoic acid and 150 ml of thionyl chloride was heated at reflux for 3 hrs. The excess thionyl cloride was removed by vacuum distillation to give 53.5 g of an amber colored liquid.

B. 2,4,6-Trimethylbenzamide

Anhydrous ammonia was added to a solution containing 53.5 g (0.29 mole) of 2,4,6-trimethylbenzoyl chloride in 500 ml of AR chloroform until thoroughly saturated. A temperature of 15° was maintained through the 10 min. addition. Continued to stir for 10 min. before filtering. The air-dried product was triturated in cold, distilled water for 30 min., then filtered and oven-dried (60°) to give 28 g. One recrystallization from 400 ml of methanol, with Darco, gave 20.5 g, m.p. softens 189°, melts 191°–194°.

C. N-[Dichlorophosphinyl]-2,4,6-trimethylbenzamide

A suspension of 21 g (0.13 mole) of 2,4,6-trimethylbenzamide and 26.8 g (0.13 mole) of phosphorus pentachloride in 200 ml of AR carbon tetrachloride was heated at 70° for 30 min. The solution was cooled to 30° and 6.1 g (0.13 mole) of 97% formic acid added dropwise. Stirred for another 20 min., then filtered, washed with AR carbon tetrachloride and air-dried to give 20.5 g, m.p. 109°–110°.

D. N-[Diaminophosphinyl]-2,4,6-trimethylbenzamide

To a suspension of 20.5 g (0.07 mole) of N-[dichlorophosphinyl]-2,4,6-trimethylbenzamide in 200 ml of AR chloroform was added 12.5 g (0.7 mole) of anhydrous ammonia. Maintained a temperature of 0°. The reaction was stirred 20 min. following the addition, then filtered, washed with cold water and air-dried to give 14.2 g, m.p. decomposes 259°–400°. Recrystallized two times from methanol, with Darco, to yield 6.1 g (36%), m.p. softens 209°, darkens, decomposes to 400°.

Anal. Calcd. for $C_{10}H_{16}N_3O_2P$: C, 49.79; H, 6.69; N, 17.42. Found: C, 49.75; H, 6.73; N, 16.89.

EXAMPLE XXIII

N-[Diaminophosphinyl]-2-furancarboxamide

A. N-[Dichlorophosphinyl]-2-furamide

A mixture of 11.1 g (0.1 mole) of furamide, 20.8 g (0.1 mole) of phosphorus pentachloride and 150 ml of AR carbon tetrachloride was heated at 70° for 30 min. or until the HCl gas evolution had ceased. Cooled to 30° and 4.7 g (0.1 mole) of 97% formic acid was added dropwise. Stirring was continued for 45 min., before filtering. The product was washed with AR carbon tetrachloride and air-dried to give 17.8 g, m.p. softens 83°, melts 93°–112°.

B. N-[Diaminophosphinyl]-2-furancarboxamide

To a suspension of 40 g (0.18 mole) of N-[dichlorophosphinyl]-2-furamide in 500 ml of AR chloroform was added at 0° over 30 min. 30.7 g (1.7 mole) of anhydrous ammonia. The precipitate was collected by filtration after stirring for 60 min., washed with cold water and air-dried to give 23 g, m.p. melts 161°–164°, complete 171°. Recrystallized from 100 ml of distilled water, with Darco, to yield 6.0 g (18%), m.p. softens 159°, melts 163°, solidifies, melts 200°–205°.

Anal. Calcd. for $C_5H_8N_3O_3P$: C, 31.75; H, 4.26; N, 22.22. Found: C, 31.79; H, 4.38; N, 22.32.

What is claimed is:

1. A compound of the formula:

wherein R is 3-pyridyl, 2-furyl, 2-naphthyl, cinnamenyl, benzyl, phenyl or phenyl substituted by 3- or 4-nitro, 4-halo, 4-amino, 4-(lower)alkoxy, 4-(lower)alkyl, 2-methyl, 2,3-dimethyl, 2,4,6-trimethyl, 3-trifluoromethyl, 4-cyano, 4-phenyl, or 3-phenoxy.

2. The compound N-[diaminophosphinyl]benzamide.
3. The compound N-[diaminophosphinyl]-3-pyridinecarboxamide.
4. The compound N-[diaminophosphinyl]-4-nitrobenzamide.
5. The compound N-[diaminophosphinyl]-4-fluorobenzamide.
6. The compound N-[diaminophosphinyl]-4-aminobenzamide.
7. The compound N-[diaminophosphinyl]-4-chlorobenzamide.
8. The compound N-[diaminophosphinyl]-3-nitrobenzamide.
9. The compound N-[diaminophosphinyl]-4-methoxybenzamide.
10. The compound N-[diaminophosphinyl]-4-methylbenzamide.
11. The compound N-[diaminophosphinyl]-2-methylbenzamide.
12. The compound N-[diaminophosphinyl]-4-cyanobenzamide.
13. The compound N-[diaminophosphinyl]-3-trifluoromethylbenzamide.
14. The compound N-[diaminophosphinyl]-4-[1,1-dimethylethyl]benzamide.
15. The compound N-[diaminophosphinyl]-2-naphthalenecarboxamide.
16. The compound N-[diaminophosphinyl]benzeneacetamide.
17. The compound N-[diaminophosphinyl]-2,3-dimethylbenzamide.
18. The compound N-[diaminophosphinyl]-3-phenoxybenzamide.
19. The compound N-[diaminophosphinyl]-4-butoxybenzamide.
20. The compound N-[diaminophosphinyl]-3-phenyl-2-propenamide.
21. The compound N-[diaminophosphinyl]-4-phenylbenzamide.
22. The compound N-[diaminophosphinyl]-2,4-dimethylbenzamide.
23. The compound N-[diaminophosphinyl]-2,4,6-trimethylbenzamide.
24. The compound N-[diaminophosphinyl]-2-furancarboxamide.

* * * * *